United States Patent [19]

Gerber et al.

[11] Patent Number: 4,863,728

[45] Date of Patent: Sep. 5, 1989

[54] MONOCLONAL ANTI-ALPHA-AMYLASE ANTIBODY WHICH NON-SPECIFICALLY INHIBITS THE ENZYME ACTIVITY OF HUMAN ALPHA-AMYLASE

[75] Inventors: Martin Gerber, Weilheim-Unterhausen; Kurt W. Naujoks, Gauting, both of Fed. Rep. of Germany

[73] Assignee: Boehringer Mannheim GmbH, Mannheim, Fed. Rep. of Germany

[21] Appl. No.: 827,776

[22] Filed: Feb. 7, 1986

[30] Foreign Application Priority Data

Mar. 8, 1985 [DE] Fed. Rep. of Germany ....... 3508384

[51] Int. Cl.$^4$ ............................................ A61K 39/395
[52] U.S. Cl. .................................. 424/85.8; 530/387; 514/21; 435/201
[58] Field of Search ................. 435/68, 240.26, 240.27, 435/172.2, 201, 948; 424/85, 85.8; 514/21; 530/387

[56] References Cited

U.S. PATENT DOCUMENTS

| | | | |
|---|---|---|---|
| 4,102,747 | 7/1978 | Driscoll et al. | 435/22 |
| 4,120,950 | 10/1978 | Homma | 530/387 |
| 4,145,527 | 3/1979 | Burns | 436/4 |
| 4,233,403 | 11/1980 | Menson | 435/22 |
| 4,376,110 | 3/1983 | David et al. | 436/513 |
| 4,544,631 | 10/1985 | Rauscher et al. | 435/14 |
| 4,622,295 | 11/1986 | Ikenaka et al. | 435/22 |
| 4,623,714 | 11/1986 | Veitesy et al. | 530/324 |
| 4,649,108 | 3/1987 | Blair | 435/22 |

OTHER PUBLICATIONS

Gerber et al., "Specific Immumoassay of α-Amylase Isoenzymes in Human Serum", Clin. Chem. v. 31(8), 1331–1334, 1985.

Dahlbäck et al., "The Non-Specific Enhancement of Allergy", Allergy, vol. 38, 261–271, 1983.

Langley et al., "Comparative Effects of Antisera to Human Pancreatic α-Amylase on Serum Amylases of Several Mammalian Species", Comp. Biochem. Physiol., vol. 55B, 563–565, 1976.

Kohler et al., "Continuous Cultures of Fused Cells Secreting Antibody of Predefined Specificity," Nature, vol. 256, pp. 495–497, 1975.

Wallenfells et al., Carb. Res. 61: 359–368, (1978).

*Primary Examiner*—Charles F. Warren
*Assistant Examiner*—Gail F. Knox
*Attorney, Agent, or Firm*—Felfe & Lynch

[57] ABSTRACT

The present invention provides a monoclonal anti-alpha-amylase antibody which non-specifically inhibits the enzyme activity of human alpha-amylase by more than 90%.

The present invention also provides a process for obtaining this monoclonal antibody and a medicament containing it.

5 Claims, No Drawings

MONOCLONAL ANTI-ALPHA-AMYLASE ANTIBODY WHICH NON-SPECIFICALLY INHIBITS THE ENZYME ACTIVITY OF HUMAN ALPHA-AMYLASE

The present invention is concerned with a monoclonal anti-alpha-amylase antibody which non-specifically inhibits the enzyme activity of human alpha-amylase.

Alpha-amylases (1,4-alpha-glucanohydrolases, EC 3.2.1.1) split 1,4-alpha-glucosidically-linked polysaccharides to give maltose and maltooligosaccharides. In the case of humans, alpha-amylase is formed in the salivary glands (h-S-A) and in the pancreas (h-P-A). It serves to digest the highly polymeric starches ingested with the nutrition to give small fragments which are then split by further enzymes to give glucose. The glucose formed is transported by the blood circulation to the energy-consuming organs.

The glucose content of the blood is regulated by insulin. If this hormone is absent, as in the case of patients who suffer from diabetes mellitus, then hyperglycaemia results after the ingestion of nutrition. In order that this glucose shock is weakened and so that the patients are not too much limited in the ingestion of nutrition, it is desirable to slow down the liberation of glucose in the blood. One possibility for this would be the inhibition of the salivary and pancreatic amylases which bring about the primary digestion of carbohydrates. The adjustment of the sugar level in the blood of patients would thereby be considerably simplified.

Possible inhibitors include plant proteins from, for example, wheat germ (Biochem. Biophys. Acta 658, 397–405/1981) and proteins and peptides from microorganisms (Prepar. Biochem. 9, 293–302/1979; Agric. Biol. Chem. 44, 1679–1681/1980; Hoppe-Seyler's Z. Physiol. Chem. 362, 465–467/1981). However, these suffer from considerable disadvantages, for example a laborious and expensive isolation. Furthermore, a preincubation of inhibitor and amylase is necessary in order that the inhibition occurs.

From Comp. Biochem. Physiol., 55B, 563–565/1976, it is known that antiserum from rabbits is able to inhibit human alpha-amylase by up to 84%. These polyclonal antibodies apparently inhibit h-P-A and h-S-A. A use of such polyclonal antibodies as medicament would not be considered.

We have now, surprisingly, found that monoclonal antibodies against alpha-amylase can be produced which are able to inhibit the enzyme non-specifically by more than 90% and, therefore, are especially suitable for a medicinal use.

Therefore, the present invention provides a monoclonal anti-alpha-amylase antibody which non-specifically inhibits human alpha-amylase by more than 90%.

By non-specifically inhibiting is here to be understood that the antibody inhibits salivary alpha-amylase and pancreatic alpha-amylase to about the same extent and thus does not differentiate between these two isoenzymes. This property is important for the usefulness as a medicament. The antibody according to the present invention can also be used for the purification of salivary amylase and also of pancreatic amylase, for which purpose it is preferably used in immobilised form.

The monoclonal antibody according to the present invention preferably inhibits the isoenzymes of human alpha-amylase by 95% or more. Especially preferred are the antibodies formed by the clones 77F5 (NCACC 85022203) and 73C8 (NCACC 85022204). The above-stated percentage inhibition values refer to the commercially available alpha-amylase test with blue-coloured, high molecular weight polymeric starch substrate. In the case of lower molecular weight substrates, the corresponding inhibiting action is more than 80%. By "lower molecular weight" are here to be understood substrates with up to about 10 glucose units. The good inhibition of the reaction of lower molecular weight substrates is of importance for a therapeutic use because the high molecular weight substrates are already split by the salivary amylase and, therefore, the pancreatic amylase in the small intestine also finds present short-chained substrates.

For obtaining the monoclonal antibody according to the present invention, there can be used, according to the present invention, Balb$_c$ mice which are immunised with human salivary alpha-amylase, the B-lymphocytes from the spleen of the immunised animals are then fusioned with myeloma cells, the hybridoma cells formed are cloned, a clone comparably inhibiting salivary and pancreatic alpha-amylase is isolated and cultured and the monoclonal antibodies formed by the clone are recovered.

Immunisation preferably takes place with the concurrent administration of aluminium hydroxide and *Bordetella pertussis*. The immunisation is preferably repeated several times, good results having been obtained with a 3- to 5-fold repetition. The B-lymphocytes are obtained from the spleen by known methods. The fusion with the myeloma cells is preferably carried out according to the standard process described in J. Immol. Meth. 39, 285–308/1980. The B-lymphocytes are here preferably used in excess.

The identification of clones which form an antibody which approximately equally strongly inhibits the human isoenzymes of alpha-amylase can be carried out by the ELISA process with the use of anti-mouse antibodies. Preferably, there are used anti-mouse-Fc-gamma-antibodies, for example from sheep. By incubation with the individual supernatants of various clones and subsequent further incubation with salivary amylase-peroxidase conjugate or with pancreatic amylase-peroxidase conjugate and detection of the bound peroxidase activity with a reagent known herefor, those clones can be identified which react equally strongly with both isoenzymes. These clones are isolated and cultured. Culturing can take place in known manner either in the cell culture or by intraperitoneal administration to mice and recovery of the monoclonal antibodies from the ascites fluid.

The pure isolation of the monoclonal antibody can also be carried out according to usual methods, for example by chromatography over an anion exchanger column, such as a cellulose or agarose column modified with diethylaminoethanol groups.

As already mentioned, the monoclonal antibodies according to the present invention can be used as medicaments for the inhibition of alpha-amylase, especially in the case of diabetes mellitus. In the case of the administration of the monoclonal antibody according to the present invention, which can take place orally, the glucose liberation in the blood is substantially slowed down and, therefore, the adjustment of the sugar level in the blood is considerably simplified. Therefore, the present invention also provides a medicament which contains, as active material, a monoclonal antibody according to the present invention, possibly together with conventional therapeutic additive and confectioning agents. In the case of the medicament according to the present invention, the monoclonal antibody is preferably so encapsulated in known manner that it can pass the stomach undigested and first become effective in the small intestine where the pancreatic amylase manifests its carbohydrate splitting action. Appropriate encapsulation methods are well known and do not here require a more detailed explanation.

The following Examples are given for the purpose of illustrating the present invention:

EXAMPLE 1

Immunisation of Balb$_c$ mice with human salivary amylase

Balb$_c$ mice are immunised with 100 μg. human salivary amylase in aluminium hydroxide, together with *Bordetella pertussis*. In an about eight-week rhythm, further immunisation is carried out three to four times with, in each case, 50 μg. adjuvant. Four days before fusion, a final immunisation is carried out intravenously with 50 μg. salivary amylase in physiological sodium chloride solution.

EXAMPLE 2

Fusion of mouse spleen cells with myeloma cells

The fusion of the spleen cells with Ag8.653 (ATCC CRL 1580) or Sp2/0 (ATCC CRL 1581) myeloma cells is carried out by the standard process according to J. Immol. Meth. 39, 285–308/1980. The fusion ratio of spleen to myeloma cells is 5:1. The fusion products are seeded on to 10 24-culture dishes (from Costar) and fed with $5 \times 10^4$ peritoneal exudate cells per culture well. 3 to 4 weeks after fusion, positive primary cultures are cloned with the help of a fluorescence-activated cell sorter. The cells are placed individually into 96-Costar plates and fed with $2 \times 10^4$ peritoneal exudate cells.

EXAMPLE 3

Test for amylase-binding antibodies

In order to identify positive primary cultures or in order to ascertain the concentration and specificity of amylase-binding antibodies in the serum of immunised mice or in the culture supernatant of the hybrid cells or in ascites, there is used an ELISA test principle. For this purpose, 96-plates (Firm Nunc) are coated with sheep-anti-mouse Fcγ antibodies. For the reduction of non-specific binding, the plates are after-coated with bovine serum albumin (2% in physiological sodium chloride solution). Thereafter, the plates are incubated with the sample containing the antibody or with various dilutions thereof. The subsequent incubation is carried out with salivary amylase-peroxidase (POD) conjugate or with pancreatic amylase-peroxidase (POD) conjugate. The activity of the bound POD is determined with ABTS (2,2'-azinodi-(3-ethylbenzthiazoline-6-sulphonate) at pH 4.4 and the extinction taken as direct measure for the bound mouse antibody. Those clones which gave equally high extinctions with salivary amylase-POD and pancreatic amylase-POD are used for the ascites production and the monoclonal antibodies investigated for their inhibiting action on pancreatic and salivary amylase.

EXAMPLE 4

Production of the monoclonal antibody via mouse ascites

Female Balb$_c$ mice are injected intraperitoneally twice with 0.5 ml. pristane (EGA Chemie) at a seven day interval. Per mouse, there are inoculated intraperitoneally, in each case, about $5 \times 10^6$ hybridoma cells of the clone 77F5 or 73C8. Depending upon the cell line, after 8 to 14 days, ascites is tapped off one to three times. This is purified via a DEAE column, the pure monoclonal antibodies being obtained.

EXAMPLE 5

Test of the inhibiting action of the monoclonal antibody

The ascites which contain the monoclonal antibody to be tested is diluted with 50 mM phosphate buffer of pH 7.0 (Solution A) to give Solution B. The inhibiting action is tested on salivary amylase and pancreatic amylase solutions with a concentration of about 1000 U/l. and about 2000 U/l. (determined with commercially available amylase reagent of Boehringer Mannheim, Cat. Order No. 568589, at 37° C.). The amylase solutions and, in each case, two controls, are pre-mixed:

I: 100 μl. amylase solution + 20 μl. Solution B
II: 100 μl. amylase solution + 20 μl. Solution A
III: 100 μl. Solution A + 20 μl. Solution B The mixtures are shaken for 10 minutes and thereafter 25 μl. of the mixture are added, in each case, to 1000 μl. of a commercially-available reagent for the determination of alpha-amylase with 4-nitrophenylmaltohaptaoside (Boehringer Mannheim, Cat. Order No. 568589). The activity is determined at 37° C. according to the manufacturer's instructions. The residual activity is calculated according to the following equation:

$$\text{residual activity (\%)} = \frac{\text{activity I} - \text{activity III}}{\text{activity II}} \times 100$$

The residual activities amount with human salivary and human pancreatic amylase, not only in the case of an activity of about 1000 U/l. but also of one of about 2000 U/l., to 15% to 20%, i.e. the inhibiting action of the MAB's amount to 80% to 85%.

EXAMPLE 6

Test of the inhibiting action of the MAB's with colored starch as substrate

The human salivary amylase and human pancreatic amylase solutions are, according to Example 5, mixed with the ascites samples which contain the MAB's to be tested and the Solutions A and B and thereafter shaken for 10 minutes. 50 μl. of the mixtures I, II and III are used in a commercially-available alpha-amylase test with blue-coloured, high polymer starch substrate (Pharmacia Diagnostics AB, Uppsala, Sweden, Cat. Order No. 93-986-2-1393-02) and, according to the manufacturer's instructions, determined at 37° C. The residual activity is calculated as in Example 5. With human salivary amylase and with human pancreatic amylase, it amounts to 5%. Thus, the inhibition rate with the high polymeric substrate is 95%.

We claim:

1. Monoclonal antibody to human salivary alpha amylase which inhibits enzyme activity of both human salivary alpha amylase and human pancreatic alpha amylase by more than 90% as measured by activity of said human salivary alpha amylase and pancreatic alpha amylase on a high molecular weight polymeric starch substrate and more than 80% as measured by activity of human alpha amylase on a substrate having 10 glucose units or less.

2. Monoclonal antibody of claim 1, wherein said monoclonal antibody inhibits enzyme activity of both human salivary alpha-amylases activity by 95% or more as measured by activity of human alpha-amylase on a high molecular weight polymeric starch substrate.

3. Monoclonal antibody 77F5, NCACC 85022203.

4. Monoclonal antibody 73C8, NCACC 85022204.

5. Composition comprising a monoclonal antibody of claim 1 and a therapeutic additive or confectioning agent.

* * * * *